United States Patent [19]

Knifton

[11] 4,111,952

[45] Sep. 5, 1978

[54] PROCESS FOR PREPARING LOWER LACTAMS FROM ALLYLIC AMINE SUBSTRATES

[75] Inventor: John F. Knifton, Austin, Tex.

[73] Assignee: Texaco Inc., New York, N.Y.

[21] Appl. No.: 745,018

[22] Filed: Nov. 26, 1976

[51] Int. Cl.$^2$ .................. C07D 201/02; C07D 207/26
[52] U.S. Cl. .................. 260/326.5 FN; 260/326.5 FL
[58] Field of Search ............ 260/326.5 FL, 326.5 FN

[56] References Cited

U.S. PATENT DOCUMENTS 3,637,743  1/1972  Prince .................. 260/326.5 FN

FOREIGN PATENT DOCUMENTS 1,027,949  5/1966  United Kingdom .......... 260/326.5 FL

*Primary Examiner*—Jose Tovar
*Attorney, Agent, or Firm*—Thomas H. Whaley; Carl G. Ries; Bernard Marlowe

[57] ABSTRACT

This invention concerns processes for preparing cyclic, 5-membered ring, lactams through the carbonylation of allylic substrates in the presence of rhodium catalysts.

10 Claims, No Drawings

PROCESS FOR PREPARING LOWER LACTAMS FROM ALLYLIC AMINE SUBSTRATES

SUMMARY OF THE INVENTION

This invention relates to the catalytic conversion of allylic substrates to cyclic lactam products.

More particularly, this invention concerns processes for the synthesis of cyclic, 5-membered ring, lactams and their homologues through the carbonylation of allylic substrates, containing three or more carbon atoms, with carbon monoxide, in the presence of a catalytic amount of a homogeneous or heterogeneous rhodium catalyst, at elevated reaction conditions of temperature and pressure. Two classes of allylic substrate may be employed in the inventive process, namely allylic amine substrates and allylic halides. Where the allylic substrate is an allylic halide, lactam synthesis is carried out in the presence of an amine coreactant selected from the group consisting of ammonia or a primary amine of 1 to 12 carbon atoms.

BACKGROUND OF THE INVENTION

It is well documented in the literature that unsaturated compounds containing a nucleophilic group and a reactive hydrogen atom in a position which favors ring closure may react with carbon monoxide to give cyclic (ring) derivatives. This invention concerns the synthesis of 5-membered ring lactams and their homologues through the metal catalyzed carbonylation of allylic substrates. The inventive process, as described therein, may be illustrated by the carbonylation reaction of equation (1) set forth below:

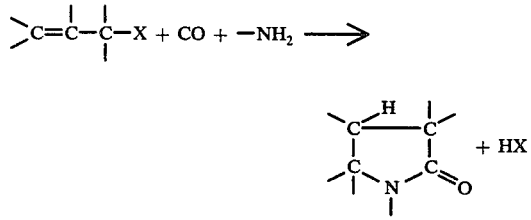

(1)

wherein the desired product is a 5-membered ring lactam, the carbon valencies indicated are satisfied by hydrogen or alkyl, cycloalkyl, aryl, alkaryl or aralkyl groupings, each containing up to 12 carbon atoms, and X may be a halogen, chloride, bromide or iodide.

Alternatively, lactam synthesis may be effected from allylic amine substrates, as set forth in equation (2), wherein again the carbon valencies indicated are satisfied by hydrogen or alkyl, cycloalkyl, aryl, alkaryl or aralkyl groupings, each containing up to 12 carbon atoms.

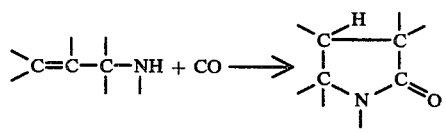

(2)

The practice of this invention, as set forth in equation (1) and (2) is illustrated by:

(1) The preparation of γ-butyrolactam from allylamine (2) The synthesis of γ-butyrolactam from allylic halides in the presence of carbon monoxide and ammonia.

(3) The synthesis of alkyl-substituted-γ-butyrolactams from allylic halides in the presence of carbon monoxide and primary alkylamines.

The lactam products of this reaction are useful generally as organic intermediates. γ-Butyrolactam, and its homologues, for example, may be important in the manufacture of polyamides, and as solvents for the separation of aromatic, aliphatic mixtures.

The preparation of lactams from allylic precursors using metal carbonyl or carbonyl precursors as catalysts in the literature*. Reviews by Falbe** and others summarize this work, particularly the synthesis of 5-membered ring lactams catalyzed by soluble cobalt catalysts. Unfortunately, many of these metal catalysts of the prior art have the intrinsic disadvantages of requiring stringent reaction conditions, particularly allylic isomerization and polymerization reactions. Furthermore they exhibit poor selectivity to the desired product and require the use of allylic amines as the allylic precursor (equation 2).

*J. Falbe and F. Korte, Chem. Ber. 98, 1928 (1965).
**"Carbon Monoxide in Organic Synthesis" by J. Falbe, Chapter IV, (1970).

This invention is directed to the use of certain homogeneous and heterogeneous rhodium catalysts which exhibit improved performances in the synthesis of 5-membered ring lactams, and their homologues, from allylic precursors. In practice this class of rhodium catalyst allows lactam synthesis under significantly milder conditions of temperature and pressure than has hitherto been possible with other metal carbonyl catalysts of the prior art, e.g. cobalt carbonyl catalysts. Furthermore, the rhodium catalysts of this invention allow the formation of lactams in higher yields, with improved selectivities to desired product and higher catalyst turnover numbers than has been practical in the prior art. A further demonstrated advantage of these rhodium catalysts is that used catalyst samples remain active after carbonylation of an allylic substrate is complete. Consequently, the used catalyst may be recycled with additional quantities of allylic substrate while demonstrating similar specific carbonylation activity to fresh catalyst material.

In the broadest practice of this invention, cyclic lactam products are produced from allylic precursors by the addition of carbon monoxide to an allylic material in the presence of a catalytic amount of rhodium catalyst, under elevated temperatures and pressures, in an oxygen-free environment, until the formation of the desired lactam products has taken place.

In the narrower practice of this invention, 5-membered ring lactams and their homologues, containing at least 4 carbon atoms, are produced by the catalytic reaction of carbon monoxide with an allylic halide by a process comprising the following steps:

(a) Admixing each mole of allylic halide to be carbonylated with at least a stoichiometric amount of an amine coreactant selected from the group consisting of ammonia or a primary amine, and at least a catalytic amount of homogeneous or heterogeneous rhodium catalyst, in the presence of a pressurized carbon monoxide atmosphere, to form a reaction mixture, and (b) Heating said pressurized reaction mixture to 20° C and above until substantial carbonylation of the allylic halide to the desired cyclic lactam derivative has taken place and isolating said desired γ-lactam contained therein.

A further embodiment of the above described invention is the preparation of 5-membered ring lactams and their homologues containing at least 4 carbon atoms by a process comprising the following steps:

(a) Admixing each mole of allylic amine to be carbonylated with at least a catalytic quantity of a homogeneous or heterogeneous rhodium catalyst in the presence of a pressurized atmosphere of carbon monoxide, to form a reaction mixture, and (b) Heating said pressurized reaction mixture to 20° C and above until substantial carbonylation of the allylic halide to the desired cyclic lactam derivative has taken place and isolating said desired γ-lactam contained therein.

In order to further aid in the understanding of this invention, the following additional disclosure is submitted:

PROCESS SEQUENCE AND VARIATIONS

In general, the components of the carbonylation reaction mixture, including optional inert solvent, allylic substrate, amine coreactant and rhodium catalyst may be added in any sequence as long as good agitation is employed throughout. The following represent some variation insofar as the mode of catalyst addition is concerned, without departing from the inventive concept. These modifications include:

(a) The catalyst may be preformed and added preformed to the mixture of the other components to form the reaction mixture.

(b) A substantial process variation that can be employed is when the catalyst is formed in situ in one or more components of the reaction mixture.

RHODIUM CATALYST

The use of a rhodium catalyst system is essential to the inventive carbonylation process. Either heterogeneous or homogeneous reaction mixtures may be employed in the practice of this invention. In the preferred embodiment, rhodium complex catalysts which are soluble in the reaction mixture give good results. However, lactam synthesis may also be effected with catalysts which are not homogeneously distributed throughout the reaction mixture. Solid catalysts which remain in place during the course of reaction may be employed and suspensions of liquid and solid catalysts in the liquid media may also be employed. In suitable embodiments of this invention the rhodium complex compound can be used in combination with inert material or contained or deposited on porous supports such as alumina, silica-alumina, activated charcoal, titania, zirconia, zeolites as well as zeolitic molecular sieves. A preferred class of inert support for the rhodium catalysts of this invention are inert porous organic polymers.

The active form of the rhodium complex catalyst may be preformed prior to carbonylation, or it may be generated in situ. Illustrative of rhodium containing substrates which can be conveniently used for effecting the carbonylation of allylic substrates to lactams include rhodium salts such as rhodium acetylacetonate, rhodium acetate dimer, rhodium formate, rhodium chloride, and rhodium dicarbonyl acetylacetonate, rhodium carbonyls such as hexarhodium hexadecacarbonyl tetrarhodium dodecacarbonyl dirhodium octacarbonyl, and chlorodicarbonyl rhodium (1), rhodium complexes with Group VB donor ligands such as chlorotris (triphenylphosphine)rhodium(I), chlorocarbonylbis(triphenylphosphine)rhodium(I), triclorotris(pyridine) rhodium(III), hydridocarbonyltris(triphenylphosphine) rhodium(I), chloropentaamminerhodium(III) chloride and dichlorotetramminerhodium(III) chloride, and rhodium olefin complexes such as bis(ethylene)rhodium(I) dimer, chloro(1,5-cyclooctadiene)rhodium(I) dimer and chloronorbornadiene rhodium(I) dimer.

Another preferred class of rhodium catalysts consists of the above classes of rhodium salts and complexes bonded to inert porous supports. A particularly favored embodiment of this invention is the use of these same rhodium salts and complexes bonded to inert porous organic polymers such as polystyrene polymers, crosslinked divinylbenzene-styrene copolymers, polyethylene and polypropylene-type polymers. These polymeric species may or may not also have appended nitrogen and phosphorus functional groups.

A further useful class of rhodium catalysts for the lactam synthesis are used catalyst samples from prior preparations.

The quantity of catalyst employed is not narrowly critical and can vary over a wide range. In general the novel process is desirably conducted in the presence of a catalytically effective quantity of the active rhodium species which gives a suitable and reasonable reaction rate. Reaction proceeds when the rhodium concentration is as little as 0.01 mM, and even less. The upper limit is dictated and controlled primarily by economic factors in view of the exceedingly high costs of rhodium metal and its compounds. No particular advantages have been observed in using relatively high concentrations of rhodium catalyst.

ALLYL SUBSTRATES

As used throughout this disclosure, this term refers to two related classes of allylic substrate, namely allylic halides and allylic amines, wherein the unsaturation (double bond) in the substrate molecule is only between carbon-to-carbon atoms, and the halide or amine group is attached to the carbon atom one removed from the carbon atom of the double bond.

Suitable allylamine substrates have the general structure (A):

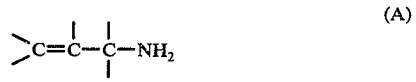

wherein the carbon valencies indicated are satisfied by hydrogen, or alkyl, cycloalkyl, aryl, alkaryl, or aralkyl groupings each containing up to 12 carbon atoms.

Illustrative of allylamines which are suitable precursors for lactam synthesis according to equation (2) include allylamine, 2-methylallylamine, 1-amino-2-decene, 1-amino-3-ethyl-2-hexene, crotyl amine, 2-amino-3-pentene and 2-amino-2-methyl-3-butene.

When an allylic halide is the primary reaction substrate then ammonia or a primary amine must also be present in the carbonylation reaction mix in order for lactam formation to be achieved as depicted in equation (1). Suitable allyl halide substrates have the general structure (B):

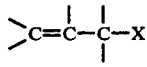

(B)

wherein the carbon valencies indicated are satisfied by hydrogen, or alkyl, cycloalkyl, aryl, alkaryl, or aralkyl groupings each containing up to 12 carbon atoms.

Illustrative of suitable allyl halide precursors for lactam synthesis according to equation (1) include allyl chloride, allyl bromide, allyl iodide, 2-methylallyl chloride, 1-chloro-2-hexene, crotyl chloride, 1-bromo-2-butene, 2-methylallyl iodide, 1-chloro-3-ethyl-2-hexene, 3-chloro-1-butene, 2-chloro-3-pentene, 1-chloro-2-decene, 3-chlorocyclohexene, and 2-chloro-2-methyl-3-butene.

AMINE COREACTANT

An amine coreactant is required whenever the lactam synthesis is from an allylic halide precursor. Suitable amine coreactants include ammonia and primary amines. Illustrative of the suitable primary amine coreactants are primary amines containing one to 12 carbon atoms, including methylamine, ethylamine, n-propylamine, cyclohexylamine, benzylamine n-hexylamine and 2-ethylhexylamine.

IODIDE PROMOTER

Where the allylic halide precursor is an allylic chloride or bromide it is preferable to add an iodide promoter to the reaction mixture, consisting of the allylic halide substrate, amine coreactant and rhodium catalyst, prior to carbonylation. Suitable iodide promoters include the alkali and alkaline earth iodides such as lithium iodide, sodium iodide, potassium iodide and calcium diiodide.

INERT SOLVENT

The carbonylation process of this invention is most conveniently carried out in the presence of a liquid diluent. Suitable diluents may be inert organic diluents, or they may be reactive diluents, including the aforementioned allylic halides, allylic amines and amine coreactants, or mixtures thereof. Illustrative of the normally liquid organic diluents which are generally suitable in the practice of this invention include, for example, saturated and aromatic hydrocarbons, e.g. hexane, octane, naphtha, cycloheptane, benzene, toluene, xylenes, naphthalenes, etc. N-Heterocyclic solvents such as quinoline, isoquinoline, lepidines, pyridine, etc. are also useful, as well as secondary and tertiary amines such as triethylamine and diethylamine. Nitriles such as acetonitrile and adiponitrile represent another class of suitable solvents for effecting the lactam synthesis.

TEMPERATURE

The temperature required for this carbonylation process is a variable dependent upon experimental factors including the allylic precursor employed, the pressure of carbon monoxide, the concentration and nature of the rhodium catalyst, among other things. Generally an operating temperature range is from 20° to 250° C when superatmospheric pressures of CO are employed.

PRESSURE

Superatmosphere pressures of at least 10 atm. are required for substantial conversion of allylamines to the corresponding γ-butyrolactams at temperatures of 20° C and above using the rhodium catalysts of this invention. Higher pressures are oftentimes employed, while at pressures less than 10 atm., carbonylation is impractically slow.

CARBON MONOXIDE ENVIRONMENT

Insofar as can be determined, the best selectivities and conversions to lactam can be obtained within a reasonable time frame by using a substantially carbon monoxide atmosphere. However, particularly in continuous operations, the carbon monoxide may be used in conjunction with from 0 to about 30% by volume of one of more inert gases such as nitrogen, argon, neon, and the like without experiencing an unacceptable decrease in yield and conversion.

REACTION TIME

The time of the reaction will vary from a very short time of a few minutes or less to 24 hours or longer, depending upon the nature of the allylic substrate, the concentration and nature of the rhodium catalyst, pressure, temperature, etc. Shorter reaction times are preferred since they give more economic processes.

CONVERSION

As defined herein, conversion is the efficiency in transforming the allylic substrate to a non-allylic product. Conversion is expressed in mole percent and is calculated by dividing the amount of allylic substrate consumed during carbonylation by the amount of allylic substrate originally charged, and multiplying the quotient by 100.

YIELD

As defined herein, yield is the efficiency in catalyzing the desired carbonylation reaction relative to other undesired reaction. In this instance the formation of a 5-membered ring lactam or lactam homologue is the desired reaction. Yield is usually expressed as mole percent, and is calculated by dividing the amount of desired lactam formed by the amount of allylic halide or amine charged and multiplying the quotient obtained by 100.

IDENTIFICATION PROCEDURES

Where applicable, the carbonylation products of this invention are identified by one or more of the following analytical procedures, gas-liquid chromatography (glc), infrared (ir), nuclear magnetic resonance (nmr) and elemental analyses. Unless specified all percentages are by weight rather than by volume and all temperatures are in centigrade rather than fahrenheit.

Having described the inventive process in general terms, the following examples are submitted to supply specific and illustrative embodiments.

EXAMPLE 1

Synthesis of γ-Butyrolactam From Allylamine OF γ-BUTYROLACTAM FROM ALLYLAMINE

Part A

To a degassed sample of allylamine (125 mmole) and toluene (75 ml) contained in a glass-lined reactor equipped for pressurizing, heating, cooling and means of agitation is added, under a nitrogen environment, 1.25 mmole of the rhodium salt, chlorocarbonylbis(triphenylphosphine) rhodium. The reactor is sealed, flushed with CO and pressured under carbon monoxide (100 atm) while heating the agitated mixture to 120° C. Pressure is adjusted to 136 atm with CO and the mixture held at temperature for 2 to 12 hours. At the end of this time, carbonylation is terminated by rapid cooling and venting of the reactor. The crude product is filtered, distilled under reduced pressure (1–10 mm Hg) to remove toluene solvent and fractionally distilled to recover the γ-butyrolactam.

The crude liquid product is analyzed by GLC. Typical conversion and yield data are as follows:

| | |
|---|---|
| Allylamine conversion | 95 mol. % |
| γ-Butyrolactam yield | 67 mol. % |
| Liquid recovery | 99% |

Samples of γ-butyrolactam were also recovered by preparative glc, and identified by a combination of nmr, ir, mass spec and elemental analyses.

| | | | |
|---|---|---|---|
| Calcd. for $C_4H_7NO$: | %C = 56.5 | | %H = 8.3 |
| Found: | %C — 56.6 | | %H = 8.4 | ir C=O, 1685 $Cm.^{-1}$, N-H, 3240 $Cm^{-1}$
$1_Hnmr(CDCl_3)$ & 7.25(s,1H), 3.42(t,2H), 2.25(t.2H), 2.13(m,2H)

Part B

The synthesis of ν-butyrolactam is carried out substantially as described in Part A except the reaction temperature is 80° C, and the reaction time 24 hours. γ-Butyrolactam is detected in the liquid product following completion of the carbonylation step.

Part C

The synthesis of γ-butyrolactam is carried out substantially as described in Part A except the operating pressure of carbon monoxide is 50 atm. Again ν-butyrolactam is detected in the liquid product following completion of the carbonylation step.

EXAMPLES 2 to 11

Synthesis of ν-Butyrolactam From Allylamine Using Other Rhodium Catalysts

Using the same type of apparatus and techniques of Example 1, ν-butyrolactam is prepared from allylamine in the presence of a variety of homogeneous and heterogeneous rhodium catalysts. These catalysts include chlorobis(ethylene)rhodium(I) dimer, chlorotris(triphenylphosphine)rhodium(I), chlorocarbonylbis(triphenylphosphine)rhodium(I), rhodium tris(acetylacetonate) rhodium chloride and rhodium chloride in the presence of excess triphenylphosphine. Active heterogeneous rhodium catalysts include rhodium chloride and chlorocarbonyl-rhodium bonded to styrene-divinylbenzene copolymers with appended diphenylphosphine and N-cyclic groups. Table I, which summarizes the performances of said rhodium catalysts under the specified carbonylation conditions.

Of particular note, it may be seen from the data in Table I that ν-butyrolactam is repeatedly synthesized here under conditions that are considerably milder than have been employed previously using the cobalt catalysts of the prior art*. In fact by comparing the yield data in Examples 2 to 4 it may be seen that the chlorobis(ethylene)rhodium(I) dimer actually gives higher yields of ν-butyrolactam at the lower carbonylation temperature of 150° C, rather than at the temperatures normally employed in syntheses of the prior art (ca. 260° C).

*J. Falbe and F. Korte, Chem. Ber. 98, 1928 (1965).

Styrene-divinylbenzene polymers are diphenyl phosphinated and treated with the homogeneous rhodium catalyst of Examples 1 to 9, and the resulting catalysts are then evaluated for carbonylation of allylamine under the conditions of Example 1, Part A. In all cases the analytical procedures confirm the formation of the desired ν-butyrolactam product.

Table I

γ-BUTYROLACTAM SYNTHESIS FROM ALLYLAMINE

| EXAMPLE | RHODIUM CATALYST | TEMP. (° C) | PRESSURE (atm) | TIME (hr) | BUTYROLACTAM YIELD (MOL%)[a] |
|---|---|---|---|---|---|
| 2 | $Rh_2Cl_2[C_2H_4]_4$ | 150 | 220 | 12 | 30 |
| 3 | " | 150 | 136 | 2 | 23 |
| 4 | " | 260 | 130 | 2 | 6.8 |
| 5 | $Rh(C_5H_7O_2)_3$b | 120 | 136 | 12 | 28 |
| 6 | $RhCl[PPh_3]_3$ | 150 | 136 | 2 | 40 |
| 7 | $Rh(CO)Cl[PPh_3]_2$ | 150 | 136 | 2 | 67 |
| 8 | $RhCl_3+2PPh_3$ | 150 | 190 | 2 | 22 |
| 9 | $RhCl_3$ | 150 | 190 | 2 | 35 |
| 10 | $RH(CO)Cl/Support^c$ | 150 | 136 | 9 | 2 |
| 11 | $RhCl_3/Support^d$ | 150 | 136 | 2 | 16 |

[a]γ-Butyrolactam yield based upon allylamine charged, estimated by glc, Solvent, Toluene or Benzene, initial $[CH_2=CH—CH_2NH_2]/[Rh]=(1-2)\times 10^2$, initial [Rh]=10-20mM.
[b]Rhodium acetylacetonate
[c]Rhodium carbonyl chloride on styrene-divinylbenzene copolymer (2% crosslinked) with appended diphenylphosphine groups.

[d]Rhodium chloride on styrene-divinylbenzene copolymer (2% crosslinked) with appended —$CH_2$—N⟨ ⟩ groups.

EXAMPLE 12

Synthesis of ν-Butyrolactam From Allylamine With Rhodium Catalyst Recycle

To a degassed sample of allylamine (125 mmole) and toluene (75 ml.) contained in a glass-lined reactor equipped for pressurizing, heating, cooling and means of agitation is added, under a nitrogen environment, 1.25 mmole of the rhodium salt, chlorocarbonylbis(triphenylphosphine) rhodium. The reactor is sealed, flushed with CO and pressured under carbon monoxide (100 atm.) while heating the agitated mixture to 120° C. Pressure is adjusted to 136 atm with CO and the mixture held at temperature for 2 hours. At the end of this time, carbonylation is terminated by rapid cooling and venting of the reactor. A small quantity (0.1 ml.) of the crude product is set aside for glc analyses, the remainder is distilled under reduced pressure (1–10 mm Hg) to remove toluene solvent and fractionally distilled to recover the ν-butyrolactam.

The residual catalyst solution is recharged to the glass-lined reactor with fresh toluene and allylamine. Carbonylation is carried out as described supra. A third and fourth sample of allylamine are carbonylated likewise using the same catalyst solution. The results are summarized in Table II.

The data serve to confirm that samples of the chlorocarbonylbis(triphenylphosphine)rhodium (I) catalyst are active for ν-butyrolactam syntheses from allylamine over at least four cycles.

Part B

The synthesis of Part A is repeated except that cobalt octacarbonyl is substituted for rhodium tris(acetylacetonate) on a mmole-per-mmole basis and the carbonylation is operated for 6 hrs at 250° C. It is evident from the run data, summarized in Table III, that the N-methyl-ν-butyrolactam is prepared from allyl chloride and methylamine using the soluble rhodium catalyst in greater than ten times the yield achieved with cobalt octacarbonyl, even where the temperature employed is higher for the cobalt case.

Part C

The synthesis of Part A is repeated except that allyl bromide is substituted for allyl chloride on a mmole-per-mmole basis. Analysis indicates that the desired N-methyl-ν-butyrolactam is present.

TABLE II

Synthesis of γ-Butyrolactam From Allylamine With Rhodium Catalyst Recycle

| Allylic Reagent | Rhodium Catalyst | Temp (° C) | Pressure (atm) | Time (hr) | Primary Lactam Product Identity | Yield (Mol %) |
|---|---|---|---|---|---|---|
| Allylamine | Rh(CO)Cl(PPh$_3$)$_2$ | 150 | 136 | 2 | γ-Butyrolactam | 67 |
| " | Recycle | " | " | " | " | 59 |
| " | Recycle | " | " | " | " | 40 |
| " | Recycle | " | " | " | " | 47 |

EXAMPLE 13

Synthesis of N-Substituted-ν-Butyrolactam From Allyl Halides

TABLE III

Synthesis of N-Substited-γ-Butyrolactame From Allyl Halide

| Reactant Charge | Rhodium Catalyst | Reaction Temp (° C) | Reaction Time (hr) | N-Methyl-γ-Butyrolactam Yield (mole %) |
|---|---|---|---|---|
| Allyl Chloride + Methylamine | Rh(C$_5$H$_7$O$_3$)$_3$ + KI | 120 | 8 | 27 |
| " | Recycle | " | 8 | 30 |
| " | " | " | 8 | 32 |
| " | " | " | 12 | 7.5 |
| | Co$_2$(CO)$_8$ | 250 | 6 | 2.0 |

Part A

To a degassed sample of allyl chloride (125 mmole) and acetonitrile (75 ml) contained in a glass-lined reactor equipped with pressurizing, heating, cooling and means of agitation is added, under a nitrogen environment, 1.25 mmole (0.58 gm) of rhodium tris(acetylacetonate) and 4.2 gm of potassium iodide. The reactor is sealed, flushed with CO, and 8 gm of methylamine (258 mmole) is pressured in from a side ampule. The pressure is adjusted with CO to 100 atm while the agitated mixture is heated to 120° C. The pressure is further adjusted to 135 atm with CO and the mixture held at temperature for 8 hrs. At this time the carbonylation is terminated by rapid cooling and venting of the reactor. A small portion (0.1 ml) of crude product is set aside for analysis, the remainder is fractionally distilled under reduced pressure (1–10 mm Hg) to recover the solvent and N-methyl-ν-butyrolactam product.

Following the fractional distillation of the crude product, the residual liquid is recharged to the pressure reactor with fresh acetonitrile solvent (75 ml), allyl chloride (125 mmole) and methylamine (8 gm, 258 mmole). Carbonylation is carried out as described supra. A third sample of allyl chloride is carbonylated in a similar manner. The results, including the lactam yield data, are summarized in Table III.

It is evident from the data summarized in this table that the rhodium acetylacetonate catalyst remains active after carbonylation and product recovery, and may be used to carbonylate additional quantities of allyl chloride to N-methyl-ν-butyrolactam.

EXAMPLE 14

Synthesis Of ν-Butyrolactam From Allyl Chloride

Part A

To a degassed sample of allyl chloride (125 mmole) and acetonitrile (75 ml) contained in a glass-lined reactor similar to Example I is added, under nitrogen, 1.25 mmole (0.58 gm) of rhodium tris(acetylacetonate) and 4.2 gm of potassium iodide. The reactor is sealed, flushed with CO, and 10 gm of ammonia (587 mmole) is pressured in from a side ampule. The pressure is adjusted with CO to 20 atm while the agitated mixture is heated to 120° C. The pressure is further adjusted to 100 atm with CO and the mixture held at temperature for 8 hours. At this time the carbonylation is terminated by rapid cooling and venting the reactor. A small portion (0.1 ml) of crude liquid product is set aside for analysis, the remainder is fractionally distilled under reduced pressure (1–10 mm Hg) to recover the solvent and ν-butyrolactam product.

Following the fractional distillation of the crude product, the residual liquid is recharged to the pressure reactor with fresh acetonitrile solvent (75 ml), allyl chloride (125 mmole) and ammonia (10 gm, 587 mmole). Carbonylation is again carried out as described supra.

Part B

The synthesis of Part A is repeated but substituting cobalt stearate for rhodium tris(acetylacetonate) on a mmole-per-mmole basis. No ν-butyrolactam is detected by glc in the crude product solution.

Part C

The synthesis of Part A is repeated but substituting cobalt octacarbonyl for rhodium tris(acetylacetonate on a mmole-per-mmole basis. No ν-butyrolactam is detected.

EXAMPLE 15

Synthesis of N-Methyl-ν-Butyrolactam from Allyl Iodide

Using the procedure and equipment of Example 13, allyl iodide (125 mmole) and acetonitrile (75 ml) and rhodium tris(acetylacetonate) (1.25 mmole) are charged to the reactor, flushed with CO and 8 gm of methylamine injected from the side ampule. The pressure is raised with CO to 50 atm while the agitated mixture is heated to 120° C. After 8 hrs the carbonylation is terminated by rapid cooling, and venting the reactor. Analysis of the crude liquid product by glc shows the presence of N-methyl-ν-butyrolactam.

As the numerous examples and preceding discussion have documented, the novel rhodium carbonylation catalysts of this invention are a significant improvement over the disclosed catalysts of the prior art, particularly regarding the yields of ν-lactams and their homologues, the relatively mild conditions of carbonylation employed, and the proven activity of the used rhodium catalyst samples upon recycle.

A further advantage of the instant invention is that while in some respects the process offers flexibility, that is, numerous modifications and changes can be made in the choice of catalyst and allylic substrate etc. without departing from the inventive concept. The metes and bounds can best be determined by reading the claims which follow in light of the preceding specification.

What is claimed is:

1. The process of preparing γ-butyrolactam or an alkyl-substituted-γbutyrolactam by the carbonylation of allylic amines having three to ten carbon atoms according to the procedure of:
    (a) Admixing said allylic amines to be carbonylated to γ-butyrolactam or an alkyl-substituted-γ-butyrolactam with at least a catalytic amount of rhodium catalyst complexes selected from the group consisting of:
    chlorobis(ethylene)rhodium(I) dimer
    Chlorotris(triphenylphosphine)rhodium(I)
    Chlorocarbonylbis(triphenylphosphine)rhodium(I)
    Rhodium tris(acetylacetonate)
    Rhodium chloride plus triphenylphosphine and
    Rhodium chloride to form a reaction mixture.
    (b) Pressurizing said reaction mixture with at least sufficient carbon monoxide to satisfy the stoichiometry of the carbonylation to the γ-butyrolactam or an alkyl-substituted-γ-butyrolactam.
    (c) Heating said pressurized reaction mixture between 20° C. and 150° C. until substantial carbonylation of the allylic amine to said γ-butyrolactam or an alkyl-subtituted-γ-butyrolactam has taken place, and isolating said γ-butyrolactam or an alkyl-substituted-γ-butyrolactam prepared therein.

2. The process of claim 1 wherein the allylic amine substrate is selected from the group consisting of allylamine, 2-methylallylamine and crotylamine.

3. The process of claim 1 wherein the rhodium catalyst is bonded to a styrene, divinylbenzene polymer appended with diphenylphosphine donor groups.

4. The process of claim 1 wherein the lactam synthesis is carried out in the presence of an inert solvent.

5. The process of claim 4 wherein the inert solvent is selected from the group of solvents consisting of aromatic solvents, aliphatic solvents, and aliphatic nitrile solvents.

6. The process of claim 1 wherein said rhodium catalyst is prepared in situ.

7. The process of claim 1 wherein said rhodium catalyst is preformed prior to the formation of the reaction mixture.

8. The process of claim 5 wherein the inert solvent is toluene.

9. The process of claim 1 wherein the allylic amine is allylamine and the lactam product is γ-butyrolactam.

10. The process of preparing γ-butyrolactam or an alkyl-substituted-γ-butyrolactam by the carbonylation of allylic amines having three to 10 carbon atoms according to the procedure of:
    (a) Admixing said allylic amines to be carbonylated to γ-butyrolactam or an alkyl-substituted-Γ-butyrolactam with at least a catalytic amount of rhodium catalyst complexes selected from the group consisting of:
    Chlorobis(ethylene)rhodium(I) dimer
    Chlorotris(triphenylphosphine)rhodium(I)
    Chlorocarbonylbis(triphenylphosphine)rhodium(I)
    Rhodium tris(acetylacetonate)
    Rhodium chloride
    said rhodium catalyst complexes are bonded to inert organic polymers selected from the group consisting of styrene, divinylbenzene polymers with appended nitrogen or phosphorus donor groups, to form a single phase reaction mixture.
    (b) Pressurizing said single phase reaction mixture with at least sufficient carbon monoxide to satisfy the stoichiometry of the carbonylation to γ-butyrolactam or an alkyl-substituted-γ-butyrolactam.
    (c) Heating said pressurized reaction mixture between 20° C. and 150° C. until substantial carbonylation of the allylic amine to said γ-butyrolactam or an alkyl-substituted-γ-butyrolactam has taken place, and isolating said γ-butyrolactam or an alkyl-substituted-γ-butyrolactam.

* * * * *